(12) United States Patent
Iwamoto

(10) Patent No.: US 6,852,354 B2
(45) Date of Patent: Feb. 8, 2005

(54) POLYMER/SUBSTRATE AND POLYMER/ POLYMER INTERFACES AND METHODS OF MODELING AND FORMING SAME

(75) Inventor: Nancy E. Iwamoto, Ramona, CA (US)

(73) Assignee: Honeywell International, Inc., Morristown, NJ (US)

( * ) Notice: Subject to any disclaimer, the term of this patent is extended or adjusted under 35 U.S.C. 154(b) by 73 days.

(21) Appl. No.: 10/113,461

(22) Filed: Mar. 28, 2002

(65) Prior Publication Data

US 2002/0157788 A1 Oct. 31, 2002

Related U.S. Application Data

(62) Division of application No. 09/543,628, filed on Apr. 5, 2000.

(51) Int. Cl.[7] .................................................. B05D 1/00
(52) U.S. Cl. ............................................................ 427/8
(58) Field of Search ............................................. 427/8

(56) References Cited

PUBLICATIONS

Iwamoto et al, Proceedings of the MRS '98 Symposium Journal: Electronic Packaging Materials Science X, 515, pp 23–20, 1998.*
Qian et al, Electronic Components and Technology Conference, pp 969–974, 1998.*
Iwamoto, N. E. "Applying Polymer Process Studies Using Molecular Modeling", Proceedings of the 4th International Conference on Adhesive Joining and Coating Technology in Electronics Manufacturing (Adhesives in Microelectronics 2000) Jun. 18–21, Helsinki, Finland; pp. 182–187.
Iwamoto, N.E. "Advancing Polymer Process Understanding in Package and Board Applications . . . ". Proceedings of the 50th Electronic Components and Technology Conference; May 21–24, 2000; Las Vegas, NV. pp. 1354–1359.
Iwamoto, N.E. "Stimulating Stress Reliability Using Molecular Modeling Methodologies". 32nd International Symposium on Microelectronics; Chicago, III; Oct. 26–28, 1999, Proceedings pp. 415–420.

* cited by examiner

Primary Examiner—Erma Cameron
(74) Attorney, Agent, or Firm—Bingham McCutchen LLP; Sandra P. Thompson

(57) ABSTRACT

A polymer/substrate and/or polymer/polymer interface is selected from candidate interfaces using a model that manipulates adhesive characteristics and strain variables, and estimates of their effect on candidate interfaces. The model is preferably used to evaluate properties such as size, shape, and bond geometries. Preferred models involve an atomic level visual representation of a first polymer adhered to either a second polymer or a substrate at the interface by a force, inclusion of strain-related information, and generating data from modeling effects on the interface of strain cycles resulting from intermittently applied force. Particularly preferred interfaces include a polymer having a monomer of the formula:

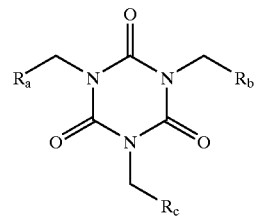

wherein $R_a$, $R_b$, $R_c$ comprises a hydroxylated aliphatic side chain; an epoxy glycol; an ethoxy ether; a glycol ether; an adduct of glycol ether and a bisphenol glycol epoxy; an adduct of an epoxy glycol and an amine such as oxydianiline to form a hydroxylamine; an adduct of a glycol ether and a cycloaliphatic epoxy such as oxybiscyclopentene oxide; an adduct of hydroxyethyl side chain and a cycloaliphatic epoxy such as oxybiscylopentene.

8 Claims, 14 Drawing Sheets

A

B

A

B

POLYMER/SUBSTRATE AND POLYMER/POLYMER INTERFACES AND METHODS OF MODELING AND FORMING SAME

This application is a divisional of pending application Ser. No. 09/543,628, filed Apr. 5, 2000.

FIELD OF THE INVENTION

The field of the invention is electronic devices and components of electronic devices, including electronic packaging materials, and materials involved in electronic packaging structures such as patches, preforms, and printed circuit boards and their materials.

BACKGROUND

Electronic devices and their components, including solder points and other interfaces, packaging materials, and printed circuit board(s), are advantageously designed to withstand at least a minimum amount of wear and tear. To determine and subsequently improve the reliability, researchers usually perform a battery of component level testing, including temperature testing, stress testing, and moisture testing.

From the mechanistic standpoint, reliability can be measured by investigating a combination of elastic, plastic, and viscoelastic behaviors of materials. For example, solder ball/underfill interface failure under may originate from a combination of plastic deformation of the solder ball and viscoelastic flow of the underfill. From that perspective reliability can be thought of as a multiple interfacial interaction with, for example, the solder-solder, polymer-polymer, polymer-solder and the associated stress/strain relationships contributing to the predicted failure.

However, for the chemist looking at polymer-involved interfaces, the determination of failure is not that simple. Failure can occur both on a relatively large level, for example from the multiple interfaces, as defined by the engineer, and also on a much smaller level from specific contributions at the atomic and molecular level. To the chemist it is the investigation of the structure at the molecular and even atomic levels that will lead to solutions of the problem. The basic concern then becomes determining the atomic and molecular causes of the failure, especially if the chemist must correct the mechanism.

From the chemist's perspective, polymer performance relies on a combination of bond-related and non-bond-related energy contributions. For instance microstructural domains, which are often studied to understand the link between morphology and engineering performance, represent a macro-scale manifestation of the energy balance originating from the molecular structure. That is, such features originate from the way in which the specific molecular structure responds to the chain structure and its relative orientation with neighboring surfaces. Orientation is also a key parameter that decides a polymer interaction, especially when looking at substrate effects in which interfacial orientation creates properties different than the bulk. So for the polymer chemist looking for the failure mechanism, several questions are always considered: a) whether the interchain interactions low enough so that only bond forces are important to the mechanical property; b) whether the through space interactions which impact orientational effects more important; or c) whether the balance of bond and through-space responses the most critical consideration to understand.

Consider the mechanism of a cycling experiment. Failure can be established by following the same mechanism as in a pure tensile or shear test. Failure can also be established and studied on the molecular level, since relative chain orientations will be constantly changing during each cycle. This change of relative chain orientations suggests that the energy drivers, which set up the orientations and the domains within that bond line, help to determine the bond strength, frequency responses and the ultimate failure. In addition, the adhesive failure depends upon the population of interfacial interactions at the surface. Failure, especially for cycling, then becomes understanding the shifting nature of the interactions that is governed by how the polymer responds to the specific stress. Network structures are even more complicated, supposedly infinite in dimension. However, given the example above, and the geometric and diffusional limits imposed on creating that infinite universe, a simple assumption can be drawn that very few highly chemically crosslinked networks actually are formed that reach from top to bottom through the bond line. It is then how the various networks interact that will form the basis of the performance of the material, whether defined as interpenetrating or entangled. The relative populations of orientations and their interactions will then help determine the survivability of the interface.

For the formulation chemist and the computational chemist then, it is the smaller universe that is addressed for performance issues. The limited assumption taken in the current studies is to understand the potential interactions of the polymer backbone. The basic drivers for structural performance to the organic chemist has always been, higher polarity, higher hydrogen bond characteristic and higher rigidity leads to higher strength. In reality, a tradeoff exists between strength, toughness, and modulus. To the computational chemist it is also clear that these tradeoffs consist of a structural balance between the bond rotational and vibrational movements, and the through space interactions or attractions that constrain local translation. Simple addition of a polar group does not always lead to a more reliable, or "stronger" interface. For the chemist, a simple correlation to structure is sought, leading to the current investigation of reliability issues on a molecular scale.

Therefore, there is still a need to reliably and repeatedly determine the likelihood and degree of failure of particular known combinations of polymers and substrates that can form an interface without excessive or undue "real-time" experimentation by the researcher. There is also a need to model and preferably predict the success and failure rates of particular combinations of novel or known classes of polymers and types of substrates that can be used to form an interface, in order to minimize futile research efforts and to minimize the costs of real-time experimentation.

SUMMARY OF THE INVENTION

In one aspect of the invention a component of an electronic device comprises a polymer having a monomer of the formula:

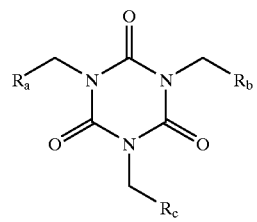

wherein $R_a$, $R_b$, $R_c$ comprises a hydroxylated aliphatic side chain; an epoxy glycol; an ethoxy ether; a glycol ether; an adduct of glycol ether and a bisphenol glycol epoxy; an adduct of an epoxy glycol and an amine such as oxydianiline to form a hydroxylamine; an adduct of a glycol ether and a cycloaliphatic epoxy such as oxybiscyclopentene oxide; an adduct of hydroxyethyl side chain and a cycloaliphatic epoxy such as oxybiscylopentene.

In another aspect of the invention a polymer/substrate and/or polymer/polymer interface is selected from candidate interfaces using a model that manipulates a set of evaluation data including a plurality of adhesive characteristics and a plurality of strain variables, and estimates of their effect on the interfaces. The model is preferably used to evaluate properties such as size, shape, and bond geometries.

In yet another aspect of the invention a computer-assisted method for generating a dynamic model of a polymer/substrate interface comprises: a) visually modeling an atomic representation of the polymer adhered to the substrate at the interface by a force; b) including molecular strain-related information into the model; and c) using the model to generate data for said polymer/substrate interface, said data including: 1) a number of strain cycles that separates the polymer from the substrate; 2) a magnitude of strain that separates the polymer from the substrate; and 3) a magnitude of the force between the polymer and the substrate.

In yet another aspect of the invention a computer-assisted method for estimating durability of an interface between a polymer and a substrate or a polymer and another polymer comprises: a) selecting a candidate combination of a polymer and a substrate or a polymer and a polymer; b) modeling the polymer and the substrate or the polymer and the polymer; c) modeling the polymer and the substrate or the polymer and polymer as being adhered to one another; d) modeling an intermittently applied force to the polymer and the substrate or the polymer and the polymer; and e) calculating a plurality of cycles of the intermittently applied force to the polymer and the substrate or the polymer and polymer that is required to disrupt the interface.

In yet another aspect of the invention a method of forming or constructing an interface between a polymer and a substrate comprises: a) modeling a plurality of structural characteristics of a plurality of candidate interfaces by quantitatively determining a strain required to separate a polymer from a substrate for each of the plurality of candidate interfaces over at least 1000 strain cycles; b) selecting a relatively superior interface from the plurality of candidate interfaces based on modeling data, the durability data and/or the evaluation data; c) obtaining a plurality of materials required to produce the polymer and the substrate; and d) using the plurality of materials to produce the polymer and the substrate; coupling the polymer and the substrate to form the interface.

DETAILED DESCRIPTION

Figure 1:
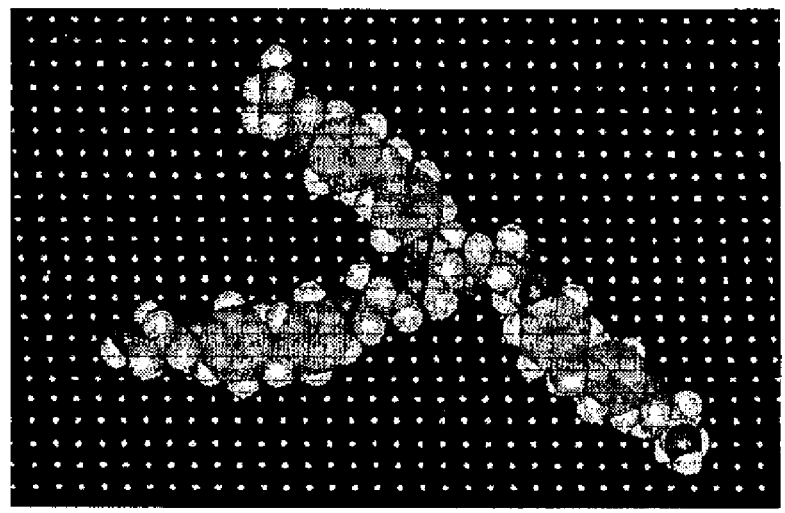
FIG. 1A is a schematic of a trimer of bisphenolA glycidyl epoxy after minimization and before forcing dynamics.
FIG. 1B is a schematic of a trimer of bisphenolA glycidyl epoxy after forcing dynamics.
Figure 1:
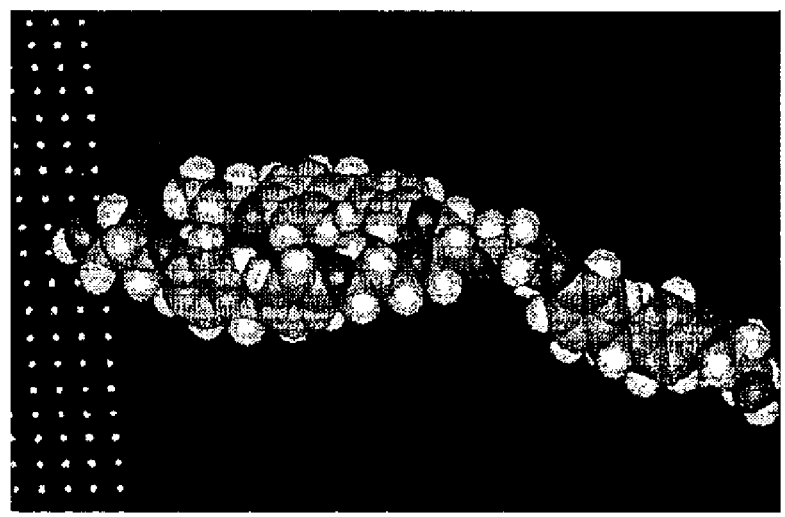

The use of polymers in electronic devices, such as computers, cell phones, televisions, appliances, and radios, has gained increasing popularity for several reasons, including that a) electronic devices have gotten smaller and more complex, b) individual components of these devices have gotten smaller and able to do more tasks, c) polymers are cheaper and easier to produce than traditional solder or interface materials, and d) polymers can be easily tailored to the particular need of the component in the device unlike traditional solder material.

Components found in electronic devices may comprise one or more types of polymers depending on the type of polymer application required in the device. A preferred electronic device includes a component or components comprising a polymer having in whole or in part a monomer of the formula:

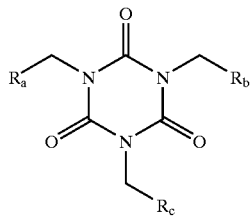

wherein $R_a$, $R_b$, $R_c$ comprises a hydroxylated aliphatic side chain; an epoxy glycol; an ethoxy ether; a glycol ether; an adduct of glycol ether and a bisphenol glycol epoxy; an adduct of an epoxy glycol and an amine such as oxydianiline to form a hydroxylamine; an adduct of a glycol ether and a cycloaliphatic epoxy such as oxybiscyclopentene oxide; an adduct of hydroxyethyl side chain and a cycloaliphatic epoxy such as oxybiscylopentene.

As used herein, the term "monomer" refers to any chemical compound that is capable of forming a covalent bond with itself or a chemically different compound in a repetitive manner. The repetitive bond formation between monomers may lead to a linear, branched, super-branched, or three-dimensional product. Furthermore, monomers may themselves comprise repetitive building blocks, and when polymerized the polymers formed from such monomers are then termed "blockpolymers". Monomers may belong to various chemical classes of molecules including organic, organometallic or inorganic molecules. The molecular weight of monomers may vary greatly between about 40 Dalton and 20000 Dalton. However, especially when monomers comprise repetitive building blocks, monomers may have even higher molecular weights. Monomers may also include additional groups, such as groups used for crosslinking.

As used herein, the term "crosslinking" refers to a process in which at least two molecules, or two portions of a long molecule, are joined together by a chemical interaction. Such interactions may occur in many different ways including formation of a covalent bond, formation of hydrogen bonds, hydrophobic, hydrophilic, ionic or electrostatic interaction. Furthermore, molecular interaction may also be characterized by an at least temporary physical connection between a molecule and itself or between two or more molecules.

Contemplated polymers that can be used as connection points or as interfaces with contemplated substrates or other components of an electronic device comprise those polymers that can withstand certain physical "stressors" included in reliability testing. Physical stressors includes any test or experiment that deforms or compromises any portion of the subject being tested, including the molecular structure of the polymer, the integrity of the interface, the structure of the component of the electronic device and/or the structure of the substrate. Preferred physical stressors include: a) the addition or subtraction of moisture to the subject, b) cooling or heating the subject, c) the application of force to the subject, d) a combination of two or more of the previous stressors. As used herein, the term "subject" means that physical manifestation or object that is being tested, including the substrate, the polymer, the polymer/substrate interface, another component of the electronic device, and the combination of the polymer, the substrate and the polymer/substrate interface.

Preferably, the components of an ideal polymer/substrate interface or polymer/polymer interface should be selected by using a model that can evaluate or select the components of a candidate polymer/substrate interface or polymer/polymer interface from a collection of candidate polymers and/or candidate interfaces. A model for evaluating a candidate polymer/substrate interface or a candidate polymer/polymer interface out of a set of or a plurality of candidate polymer/substrate interfaces or a plurality of candidate polymer/polymer interfaces should preferably comprise a) software that executes on a computer that manipulates a set of evaluation data, said evaluation data includes a plurality of adhesive characteristics, a plurality of strain variables, and estimates of their effect on the interfaces; and b) an output device operatively coupled to the computer that outputs the evaluation data.

Substrates contemplated herein may comprise any desirable substantially solid material. Particularly desirable substrate layers would comprise films, glass, ceramic, plastic, metal or coated metal, or composite material. In preferred embodiments, the substrate comprises a silicon or germanium arsenide die or wafer surface, a packaging surface such as found in a copper, silver, nickel or gold plated leadframe, a copper surface such as found in a circuit board or package interconnect trace, a via-wall or stiffener interface ("copper" includes considerations of bare copper and it's oxides), a polymer-based packaging or board interface such as found in a polyimide-based flex package, lead or other metal alloy solder ball surface, glass and polymers such as polymimide, BT, and FR4. The "substrate" may even be defined as another polymer chain when considering cohesive interfaces. In more preferred embodiments, the substrate comprises a material common in the packaging and circuit board industries such as silicon, copper, glass, and another polymer.

As used herein, the term "interface" means a couple or bond that forms the common boundary between two parts of matter or space. An interface may comprise a physical attachment of two parts of matter or components or a physical attraction between two parts of matter or components, including bond forces such as covalent and ionic bonding, and non-bond forces such as Van der Waals, electrostatic, coulombic, hydrogen bonding and/or magnetic attraction. Preferred interfaces include those interfaces that are formed with non-bond forces As used herein, the term "candidate" means that which is most preferred or most suitable for the particular situation contemplated by the researcher, for the particular requirement of the electronic device, or both.

As used herein, the term "software" means the programs, data, and routines for use with a computer, as distinguished from the physical components of the computer. Contemplated software that can be used is basic molecular modeling software. Preferred software is Insight/Discover from Molecular Simulations, Inc, 9685, Scranton Road, San Diego, Calif. 92121. As used herein, the term "computer" means an electronic device, which, by means of stored or provided instructions and information, performs rapid and/or complex calculations, compiles data, correlates data, and selects data. As used herein, the term "output device" means that device that facilitates the presentation of data to the user. As contemplated herein, an output device may include a monitor, a speaker, a printer, or a television screen. As used herein the phrase "operatively coupled" includes two or more devices coupled by any suitable means, such as coaxial cable, parallel or serial cable, or infrared.

As used herein, the term "adhesive characteristics" means those properties or characteristics that describe, define or otherwise outline the adhesive ability of an interface, including bond strength, degree of bonding, moisture content, ability of an interface to withstand a change in temperature, coulombic interactions, electrostatic interactions, Van der Waals interactions, molecular orientations, interaction volume, interaction distance, interaction dynamics, interaction energies, morphology correlations, surface structure, and network structure. As used herein, the term "strain variables" includes those variables measured from the interaction of a force with the polymer, the interface, or the substrate, and may include some of the properties or characteristics that are also investigated as "adhesive characteristics". Strain variables may also include bond types, crystal structure, amorphous structure, chain structure, degree of disruption of the interface, degree of cracking, degree of fraying, degree of separation of the polymer from the substrate or the other polymer, and degree of force applied.

Once at least one candidate polymer/substrate interface has been selected by the researcher, a model of the interface can be generated and studied to evaluate such properties as size, shape, or bond geometries. A computer-assisted method for generating a dynamic model of an interface between a polymer and a substrate comprises: a) visually modeling an atomic representation of the polymer adhered to the substrate at the interface by a force; b) computation of the energy trajectories during a modeling run; c) including molecular strain-related information into the model; and d) using the model to generate data for said polymer/substrate interface, said data including: 1) a number of strain cycles that separates the polymer from the substrate; 2) a magnitude of strain that separates the polymer from the substrate; and 3) a magnitude of the force between the polymer and the substrate.

As used herein, the term "model" means a representation or imitation of an existing object, such as a polymer, a polymer/polymer interface, a substrate, a polymer/substrate interface, an electrical device, a component of the electrical device, or any portion or segment of said representation. As used herein, the term "computer-assisted method" means that method that incorporates in whole or in part the use of a computer during the method.

As used herein, the phrase "molecular strain-related information" means that information that influences the size, shape, energy level, form of matter, or temperature of the polymer, the substrate the polymer/polymer interface, and or the polymer/substrate interface. As used herein, the term "strain cycle" means that period of time whereby a force is applied to the subjects of the model, including the polymer, the substrate, the polymer/polymer interface, and/or the polymer/substrate interface, and the subjects of the model are allowed to relax back to the original state before the force was applied.

Once a model has been generated the polymer, the substrate, the polymer/polymer interface and/or the polymer/substrate interface can be studied theoretically to determine relative durability. Durability is an important quality in the determination of a suitable polymer/polymer or polymer/substrate interface. Durability can include such qualities as a) the amount of force that the interface can withstand before being disrupted, b) the highest and lowest temperature that an interface can withstand before being disrupted, c) the degree of moisture that an interface can withstand before being disrupted, d) the amount of pressure that the interface can withstand before being disrupted.

A computer-assisted process for estimating durability of an interface between a polymer and a substrate or a polymer and another polymer comprises: a) selecting a candidate combination of a polymer and a substrate or a polymer and a polymer; b) modeling the polymer and the substrate or the polymer and the polymer; c) modeling the polymer and the substrate or the polymer and polymer as being adhered to one another; d) modeling an intermittently applied force to the polymer and the substrate or the polymer and the polymer; and e) calculating a plurality of cycles of the intermittently applied force to the polymer and the substrate or the polymer and polymer that is required to disrupt the interface.

Selection of the candidate combination of a polymer and a substrate or a polymer and a polymer can be performed by the model previously described herein or by another suitable model, method or desire, such as cost concerns, availability of materials, or other external considerations. It is preferred that the selection of the candidate combination of a polymer and a substrate or a polymer and a polymer should be performed by the model previously described herein.

Modeling the polymer and the substrate or the polymer and the polymer can be performed by the computer-assisted method previously described herein or by another suitable method, such as traditional drawings or sketches, conventional stress analysis, or another acceptable method. Modeling the polymer and the substrate or the polymer and the polymer as adhered to one another can also be performed by the computer-assisted method previously described herein or by another suitable method. It is preferred that both models should be performed by the computer-asssisted method described herein.

Modeling an intermittently applied force to the polymer and the substrate or the polymer and the polymer can be performed by applying a certain degree of force for a predetermined period of time to the polymer, the substrate, or the polymer/substrate interface; or the polymer, the other polymer or the polymer/polymer interface. The phrase "degree of force" not only includes the magnitude of the force applied but also the direction of the force applied.

Calculation of the plurality or the number of cycles of the intermittently applied force to the polymer and the substrate or the polymer and polymer that is required to disrupt the interface may be performed visually, mathematically, or by any other suitable means. The phrase "disrupt the interface" includes physical separation of the interface such as any cracking, fracturing, breaking, shearing, bubbling, or molecular breakdown of the polymer, the substrate, or the polymer/substrate interface; or the polymer, the other polymer or the polymer/polymer interface. It may also mean a lowering of the total energy of the system after a force is applied, to a point beyond reversibility from a predefined initial minimum energy state.

Once the modeling and durability experiments have been completed on the candidate polymers, substrates, polymer/polymer interfaces and/or polymer/substrate interfaces, the actual polymers, substrates, polymer/polymer interfaces and/or polymer/substrate interfaces should be constructed while taking into account the modeling, durability and evaluation data.

A method of forming or constructing an interface between a polymer and a substrate comprises: a) modeling a plurality of structural characteristics of a plurality of candidate interfaces by quantitatively determining a strain required to separate a polymer from a substrate for each of the plurality of candidate interfaces over at least 1000 strain cycles; b) selecting a relatively superior interface from the plurality of candidate interfaces based on modeling data, the durability data and/or the evaluation data; c) obtaining a plurality of materials required to produce the polymer and the substrate; and d) using the plurality of materials to produce the polymer and the substrate; coupling the polymer and the substrate to form the interface.

Selection of a relatively superior interface from a plurality of candidate interfaces comprises investigating the modeling data, the durability data and/or the evaluation data previously collected and determining the more suitable interface while keeping in mind the needs or requirements of the electrical device or individual components of the electrical device. It is contemplated that there may be one or more relatively superior interfaces based on the data. It is further contemplated that in the case of one or more relatively superior interfaces that the researcher shall make the decision on the interface based on other conditions, such as cost concerns, available materials, and ease of use.

Suitable materials that may be used to form the polymer and/or the substrate includes any chemical precursors, solvents, gases, and/or compounds that the researcher needs to construct the polymer or substrate. Contemplated chemical precursors include tris(2,3-epoxyproply)isocyanurate; 1,3,5 tris(2-hydroxyethyl)1,3,5,triazine2,4,6 t(1H,3H,5H) trione; bis(2,3 epoxycyclopentyl ether); 4,4' oxydianiline; bisphenol A glycidyl ether; bis(3,4epoxycylohexylmethyl) adipate.

Contemplated solvents include any suitable pure or mixture of organic, organometallic or inorganic molecules that are volatilized at a desired temperature, such as the critical temperature. The solvent may also comprise any suitable pure or mixture of polar and non-polar compounds. In preferred embodiments, the solvent comprises water, ethanol, propanol, acetone, ethylene oxide, benzene, toluene, ethers, cyclohexanone, butryolactone, methylethylketone, and anisole. In the preferred embodiments, no solvent is used and at least one liquid monomer is chosen to form a solventless formulation. As used herein, the term "pure" means that component that has a constant composition. For example, pure water is composed solely of $H_2O$. As used herein, the term "mixture" means that component that is not pure, including salt water. As used herein, the term "polar" means that characteristic of a molecule or compound that creates an unequal charge, partial charge or spontaneous charge distribution at one point of or along the molecule or compound. As used herein, the term "non-polar" means that characteristic of a molecule or compound that creates an equal charge, partial charge or spontaneous charge distribution at one point of or along the molecule or compound.

Contemplated gases include nitrogen, oxygen, argon, helium, hydrogen or gas mixes such as air, zero air, and argon/nitrogen. Contemplated compounds can be composed of organic, inorganic or organometallic compounds, or any suitable combination of organic, inorganic, and/or organometallic compounds, depending on the desired mechanical properties of the polymer and/or substrate. Examples of contemplated organic compounds are polyethers, polyimides, thermoset aromatics or polyesters. Examples of contemplated inorganic compounds include silica or aluminosilicates as well as ceramic materials. Examples of contemplated organometallic compounds include poly (dimethylsiloxane), poly(vinylsiloxane) and poly (trifluoropropylsiloxane). The polymer and/or substrate may also include both polymers and monomers depending on the mechanical properties and consistency desired. It is further contemplated that the polymer and/or substrate may be composed of amorphous, cross-linked, crystalline, or branched polymers.

EXAMPLES

Example 1

Molecular systems used in this study are usually constrained to oligomers or to systems no larger than around 100–200 heavy atoms per single chain and a maximum substrate surface of up to 2,000–3000 atoms, depending upon the packing density and surface area. The substrate atoms are held fixed for ease of computation. All hydrogens are included in the model calculations. These system constraints allow the maximum model size to be small enough so that an exploratory search of many different structures can be done without spending large amounts of time.

The initial assumption is simple: we assume that the highest contribution to reliability comes from the highest chain interaction configuration possible, and that this interaction will evolve from both the chain and the network structure. To approximate this assumption, we start with an oriented structure, minimize to determine a better structural fit, and either force the chains apart for cohesion insight, or off a substrate surface for adhesion insight. For this work, we do not worry about the network structure, as we are concerned about determining the best combination of group, monomer, or chain structure that will enhance chain interaction. A second assumption is also used: the lowest energy configuration of the system in study is that of the minimized form. This assumption then suggests that as the chain undergoes stress, higher energy states are being attained so that in the course of failure generation, you will always progress away from its minimum energy state. This is a reasonable assumption as the energy used to strain anything must go toward both translation and deformation.

The cycling model is done using a set strain target during a forcing step in which the polymer is pulled away from it's substrate (either another polymer chain or an inorganic surface). A relaxation step is also done, in which the polymer is allowed to equilibrate with its substrate before proceeding with the next strain step. Failure on this scale is defined by complete separation of the structures under investigation. The procedure is repeated using different strain targets. FIG. 1A and FIG. 1B shows a schematic of how a model may look is before and after cycling, near failure.

Figure 2:
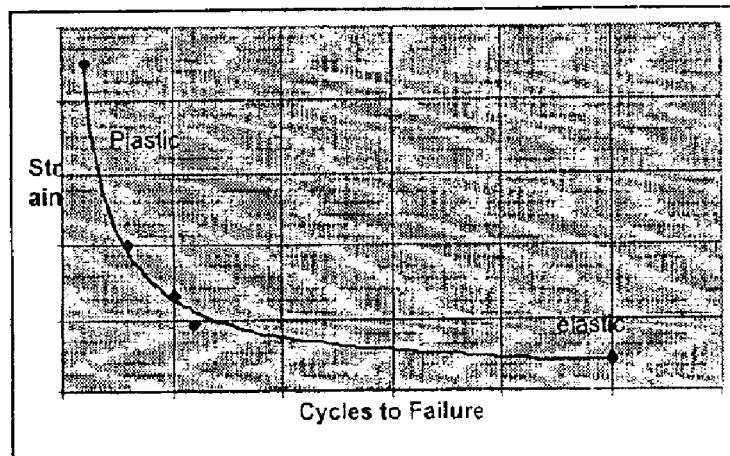
FIG. 2A is an example of a typical molecular cycling result showing Coffin-Manson response, by showing the overall response to the number of cycles.
FIG. 2B is an example of a typical molecular cycling result showing Coffin-Manson response, by showing the log transformation of the response to the number of cycles.
Figure 2:
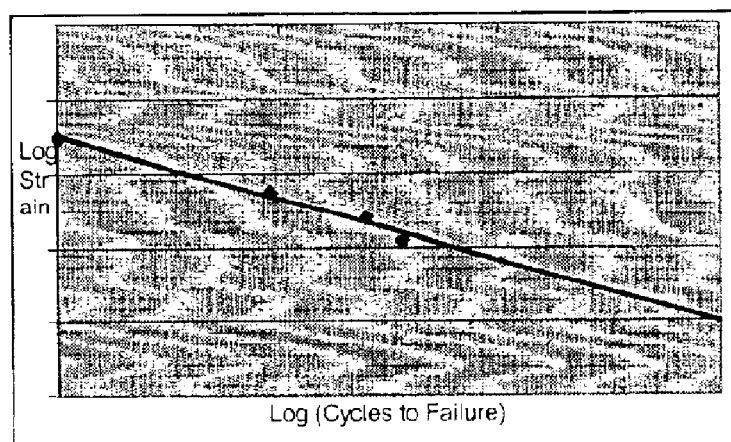

Work to date has indicated a Coffin-Manson type of response to cycling, which is shown in FIG. 2A and FIG. 2B for a typical result of the modeling. The Coffin-Manson Theory predicts a power relationship between the strain and the number of cycles. A log-log plot of strain vs. number of cycles produces a straight line from which many cycles can be extrapolated. The extrapolation is used to determine a qualitative tendency of the polymer in question to survive cycling. For the molecular cycling, this analysis is always used in a comparative way, so that relative rather than exact strain predictions are obtained. By using a similar high cycle extrapolation (for instance 500 or 1000 cycles) benchmark, formulations can be compared as to their relative tendency to survive high cycling as measured by whether a higher strain is sustained compared to the competitor. For structural analysis, all of the different interfaces in contact with a polymer may be calculated. The relative differences in the amount of strain that the different interfaces can sustain, help to pinpoint failure causes.

Results of the modeling analysis are found in FIGS. 3–9. All modeling investigated the difference between the theoretical "cohesive" (polymer/polymer interface) and the "adhesive" (polymer/substrate interface) interactions.

Figure 3:
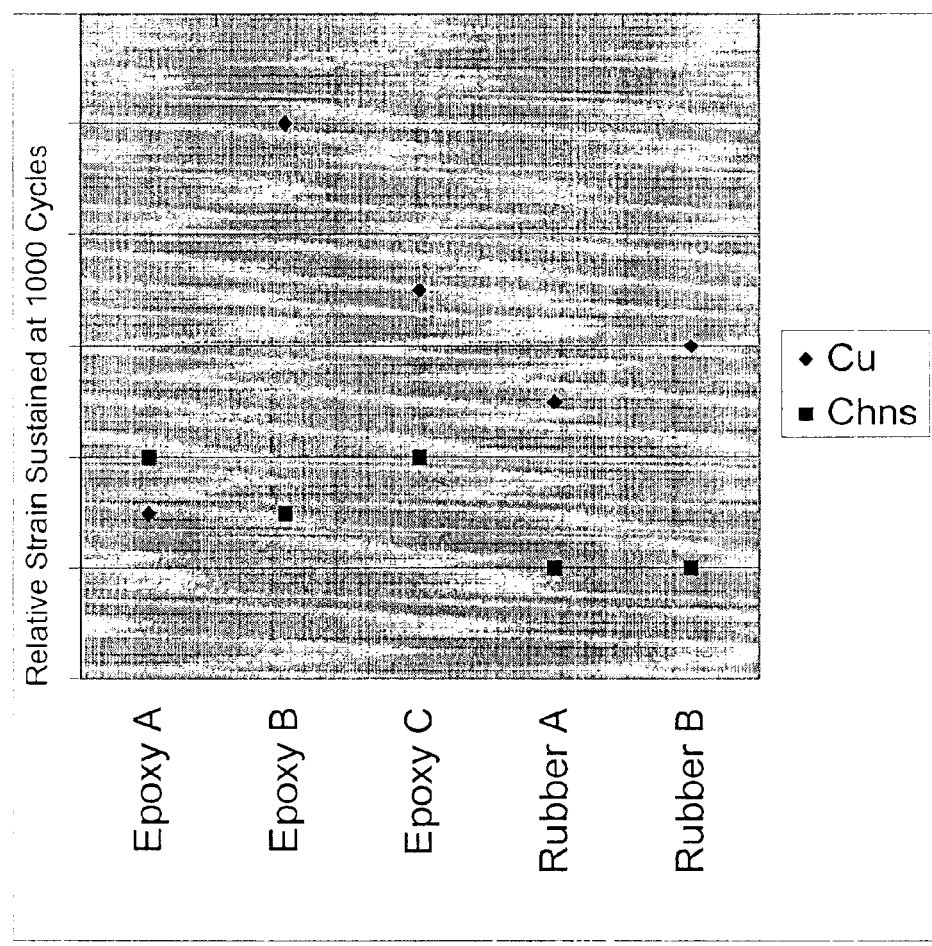
FIG. 3 is a graph of the cycling results of five different resin types contrasting performance differences for both adhesive and cohesive cases. Epoxy A is a trimer of bisphenol F glycidyl ether; Epoxy B is a trimer of cycloaliphatic epoxy; Epoxy C is a trimer of bisphenol A glycidyl ether; Rubber A is a silicone that is a copolymer of PDMS and norbornylmethylsilane; and Rubber B is polybutadiene.
Figure 4:
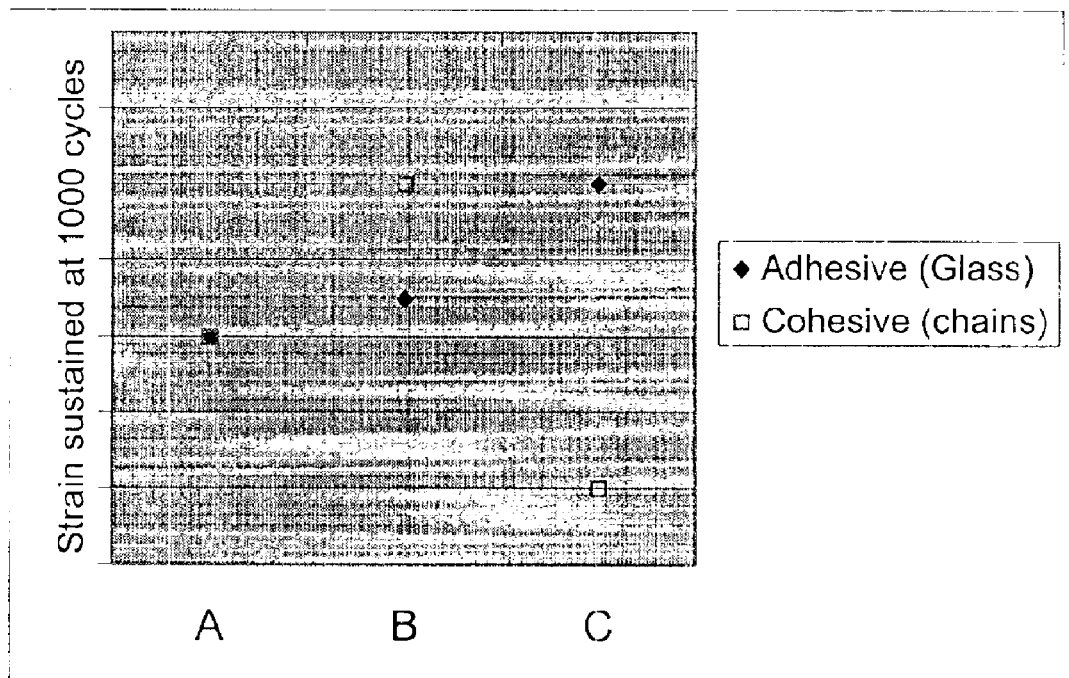
FIG. 4 is a graph of the cycling results using glass as a substrate. A is a trimer of bisphenol F glycidyl ether; B is a trimer of cycloaliphatic epoxy; C is a copolymer of PDMS and norbornylmethylsilane.

The first model studies concentrated on comparing resin types to predicted cycling tendency. FIGS. 3 and 4 show the results of this study comparing three different epoxy types and two different rubber formulations for adhesive cycling on copper and for cohesive cycling. For ease of comparison, the strain at the extrapolated 1000 cycle benchmark was used. Experimental test results on formulations made with these materials have shown that the second epoxy material ("Epoxy-B") survives thermal shock treatments the best, with the adhesive strain being highest. We have previously reported results on adhesion modeling and confirmatory experiment that indicated "Epoxy-B" had the best moisture resistance. In general, the cohesive interface is the usually the weakest interface found.

To investigate additional surfaces using the modeling technique, glass surfaces were also studied using three different formulations. The modeling results are shown in FIG. 4 indicating that formulation B has the best overall predicted cohesive and adhesive cycling performance. Although preliminary, experimental tests have indicated that the middle formulation B has better interfacial qualities and has been selected for further study in applications.

Figure 5:
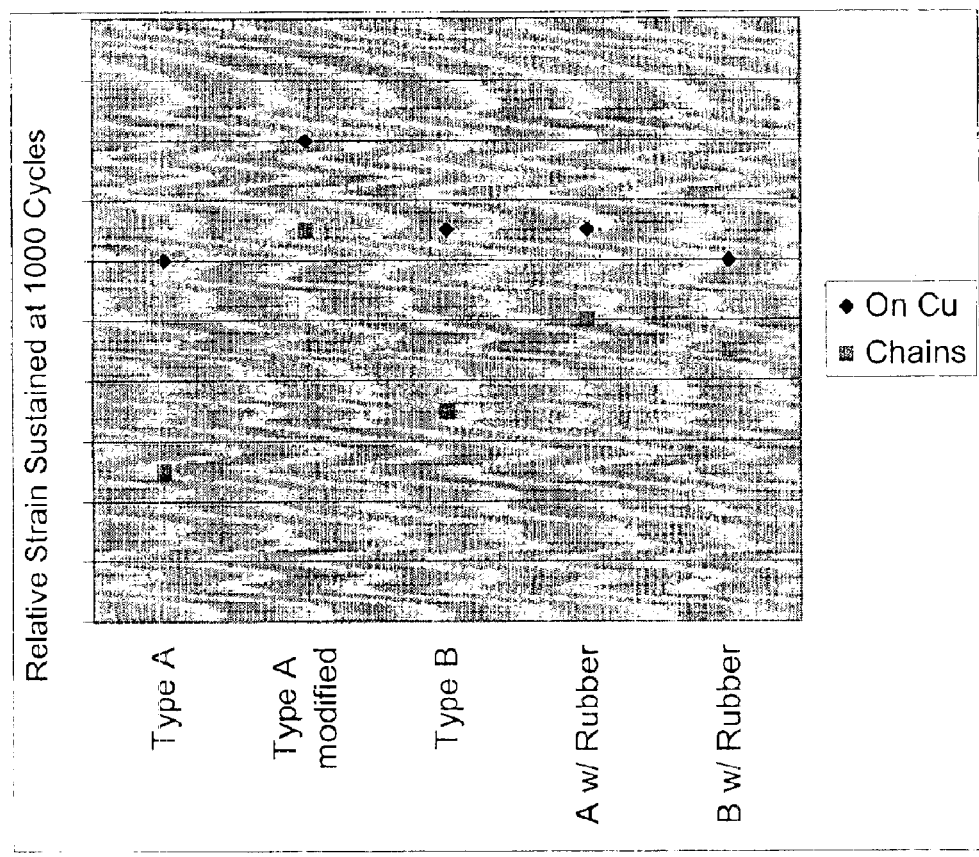
FIG. 5 is a graph of the cycling results of ongoing formulation development showing the effects of modification for the adhesive case on copper substrate and the cohesive case on polymer/polymer interface chains.

FIG. 5 shows the 1000 cycle strain intercept results for ongoing materials development using two basic formulation types. In this case copolymers of resin blends have been studied. According to the model all interfaces should fail cohesively first, having the lowest strain. However, modificaton "A" is better than the original material formulation and should help sustain both the cohesive and adhesive interface. In addition, FIG. 5 shows that rubber toughening is predicted to enhance the cohesive cycling survivability of both formulation types.

Experimentally, we have found that Modification "A" is absolutely necessary to survive cycling tests, whereas rubber toughening does not help to the same extent as the modification. Modification "A" is a common practice used in the circuit board industry in which engineers use a permanganate treatment to chemically "roughen" the surface. On a molecular scale, it can be identified as an oxidation step.

Figure 6:
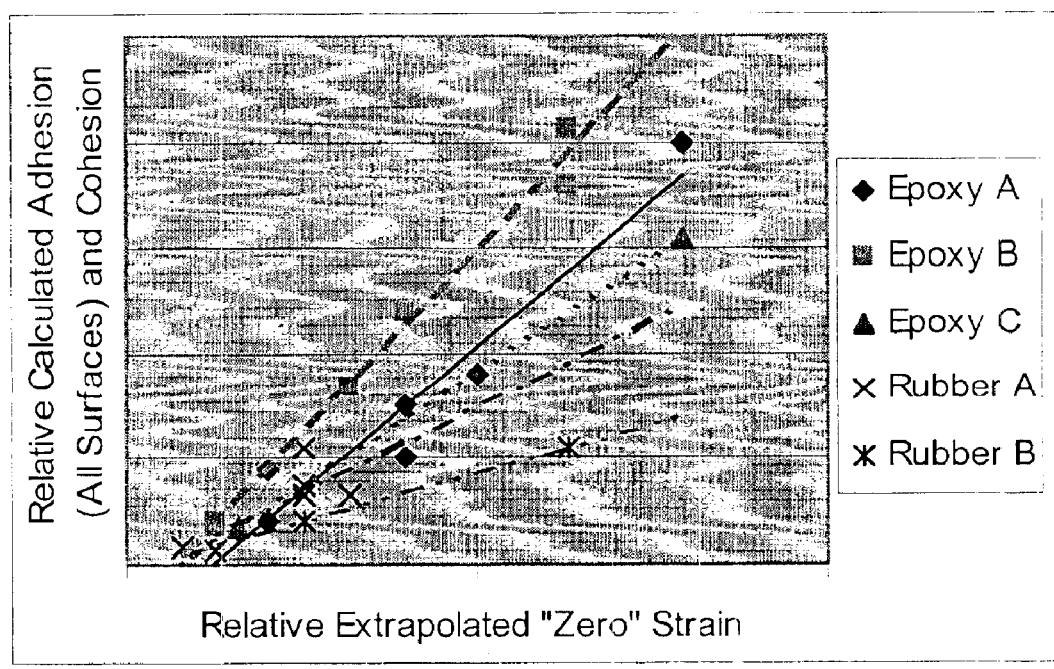
FIG. 6 is a graph of the combined adhesion and cohesion versus the "zero strain" intercept of the cycling results contrasting resin performance. Epoxy A is a trimer of bisphenol F glycidyl ether; Epoxy B is a trimer of cycloaliphatic epoxy; Epoxy C is a trimer of bisphenol A glycidyl ether; Rubber A is a silicone that is a copolymer of PDMS and norbornylmethylsilane; and Rubber B is polybutadiene.
Figure 7:
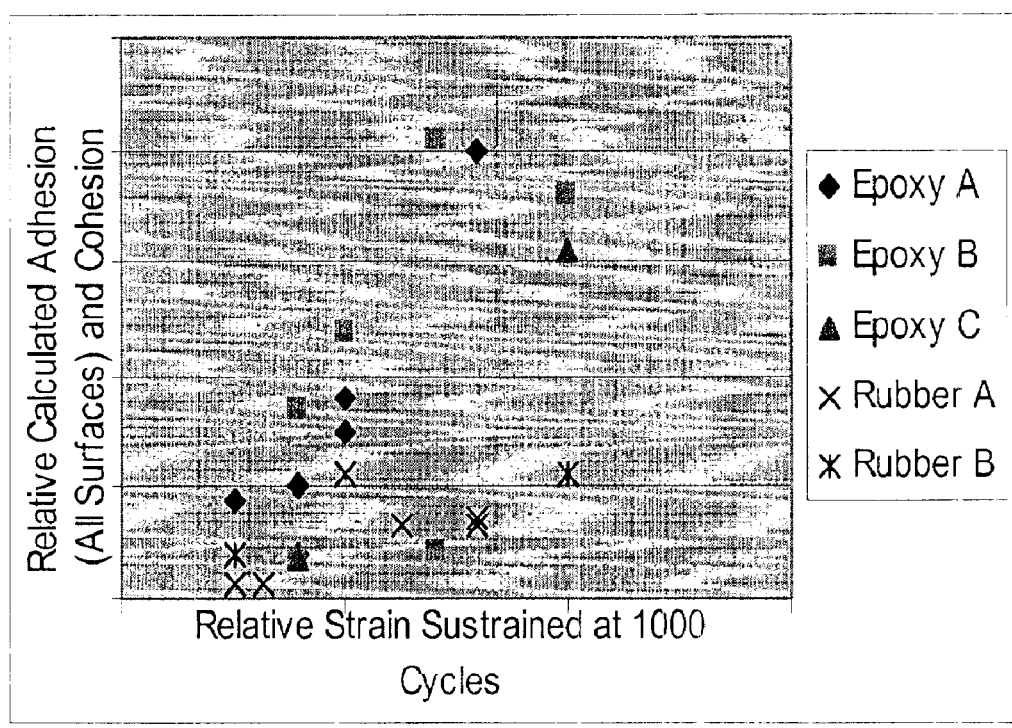
FIG. 7 is a graph of combined adhesion (polymer/substrate interface) and cohesion (polymer/polymer interface) versus "1000 cycle intercept". Epoxy A is a trimer of bisphenol F glycidyl ether; Epoxy B is a trimer of cycloaliphatic epoxy; Epoxy C is a trimer of bisphenol A glycidyl ether; Rubber A is a silicone that is a copolymer of PDMS and norbornylmethylsilane; and Rubber B is polybutadiene.

Additional analysis can give an indication of interfacial sensitivity and the relationship to adhesion (which can be thought of as a one-cycle failure test). FIG. 6 is a plot of the predicted adhesion across all of the interfaces studied and the theoretical "zero strain" intercept of the Coffin-Manson log-log plots. Interestingly, FIG. 6 suggests that a relationship may exist between the adhesion and the theoretical "zero cycle" strain (which can be thought of as the idealized maximum strain the specific interface can handle).

A marked difference between material types is found in which "Epoxy-B" has the greatest sensitivity to changes in interface type. As expected, both of the rubbers evaluated in this modeling have the lowest responses in FIG. 6 indicating that they may sustain high strain with low force.

However, because FIG. 6 is non-specific about the definition of the interface (as all interfaces are represented), FIG. 6 also argues for understanding the balance in properties necessary for failure. For example, to maintain a similar adhesive level to another material, "Epoxy-B" sustains a lower theoretical zero cycle strain and this specific interface may fail first given an adequate amount of stress is present. By contrast, the other material may be sustaining a higher strain, but this may be due to a different interfacial contribution than the one failing for "Epoxy-B". If this is a blend of the two materials this second interfacial contribution may contribute to survivability of the overall adhesive bond. For combination interfaces then, the analysis of the zero strain contributions can help pinpoint potential material or structural weaknesses.

Figure 9:
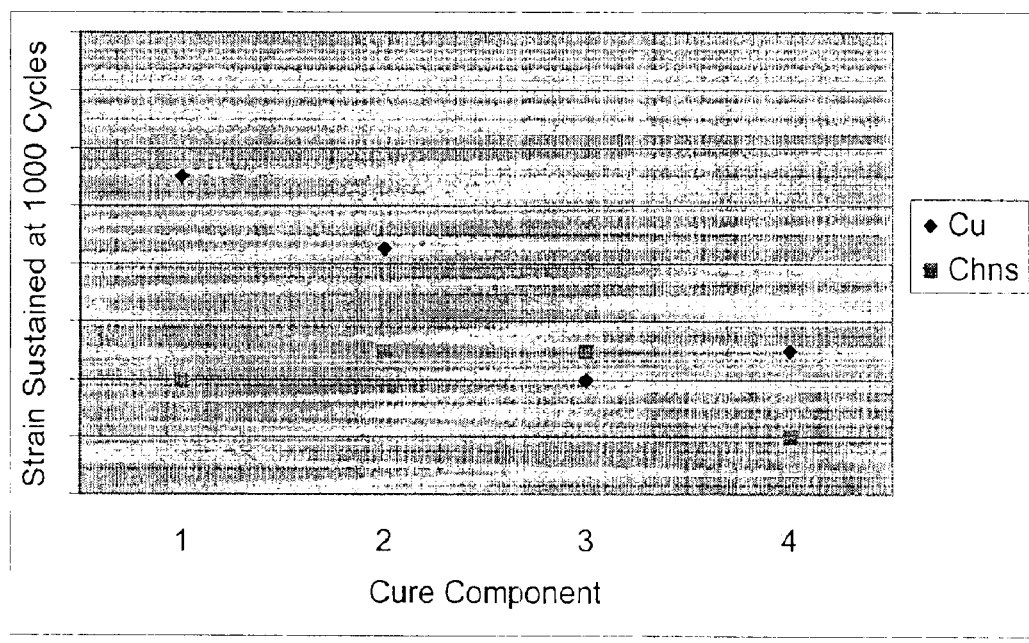
FIG. 9 is a graph of a cure component study of viafill formulation primary resins. Component #1 is a trimer of bis 3,4 epocycyclohexylmethyladipate; Component #2 is the oxaxolidinone formed from the rearranged adduct of 1,1 bis(4-cyanatophenyl) ethane and bisepoxycyclohexylmethyl adipate; Component #3 is a combination oxazolidinone and isocyanurate product derived from the rearranged adduct of 1,1 bis(4-cyanatophenyl) ethane bisepoxycyclohexylmethyl adipate; and Component #4 is the isocyanurate formed from the rearranged adduct of 1,1 bis(4-cyanatophenyl) ethane bisepoxycyclohexylmethyl adipate.

It is worthwhile to iterate that FIG. 6 says nothing about cycling ability. If a similar analysis is done for the 1000 cycle intercept (FIG. 7), no correlation is suggested between the adhesion and the strain sustained at 1000 cycles. This lack of correlation indicates a sensitivity and dependence of the cycling performance on the interfacial structure. For cycling prediction, then, each interface should be individually modeled rather than assuming high adhesion will lead to high reliability. Interestingly, just like the "zero cycle" extrapolation, both rubber models in FIG. 7 appear to have the least sensitivity to the interface (lowest points in general) which suggests they can sustain higher strains at lower energies. So the "zero cycle" strain and the 1000 cycle intercept can be used to help one distinguish between brittle or rubbery materials as shown in FIG. 9 which plots the predicted "zero" cycle strain with the 1000 cycle intercept results.

Figure 8:
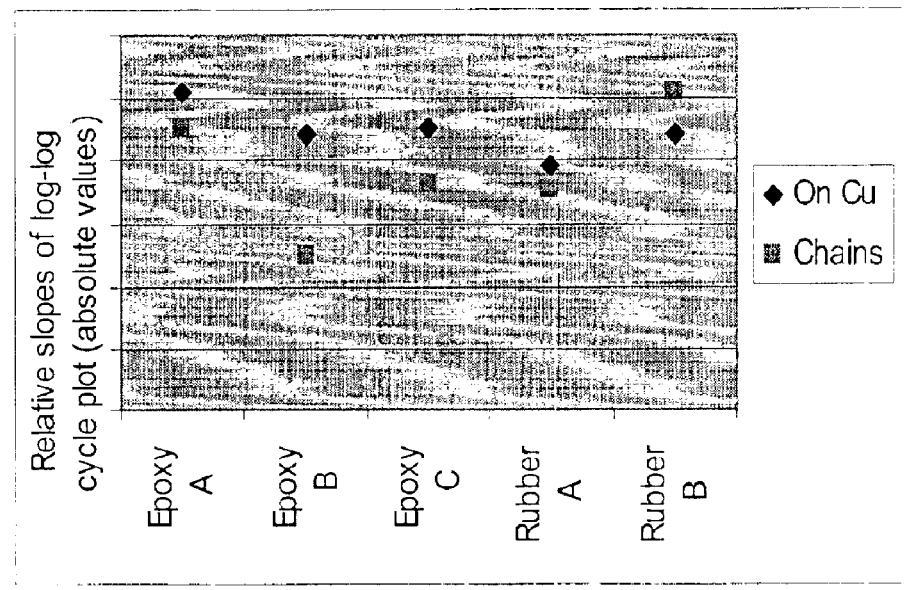
FIG. 8 is a log-log cycle plot contrasting the cycling sensitivity of five resins. Epoxy A is a trimer of bisphenol F glycidyl ether; Epoxy B is a trimer of cycloaliphatic epoxy; Epoxy C is a trimer of bisphenol A glycidyl ether; Rubber A is a silicone that is a copolymer of PDMS and norbornylmethylsilane; and Rubber B is polybutadiene.

An additional analysis of the slopes of the Coffin-Manson log-log cycle plot may also be done. This analysis helps to determine the sensitivity of the interface to the number of cycles. FIG. 8 shows the results of such an analysis for the five resin types previously mentioned. Interestingly, FIG. 8 indicates that the "Epoxy B" chains have the lowest absolute slope, showing the least sensitivity to cohesive cycling, whereas Rubber A shows the lowest adhesive sensitivity to cycling.

However, it is important to iterate that the adhesion tendencies will not be the same as the cycling abilities, as adhesion is usually as a high strain event and the cycling a lower stain event. If a similar analysis is done for the 1000 cycle intercept, no correlation is suggested between the adhesion and the strain sustained at 1000 cycles. This lack of correlation indicates a sensitivity and dependence of the cycling performance on the interfacial structure. For cycling prediction, then, each interface should be individually modeled rather than assuming high adhesion will lead to high reliability.

Taken altogether a performance profile can be drawn for the various systems studied. For example, of the epoxies, "Epoxy B" is expected to be able to sustain the highest cohesive strain with low sensitivity to the number of cycles, but have relatively high sensitivity to the interface definition. By contrast, the rubber materials may have high adhesive cycling ability sustaining higher strain, but their cohesive cycling ability is much lower than the other resins and overall their strength is lower so they will not sustain high stress. These contrasting profiles may be expected given the types of materials, but demonstrates the potential usefulness of the analysis, especially when looking at new formulations and new polymers.

An example of using the modeling results to affect formulation development can be found by referring to FIGS. 3 and 4 above. Modeling indicated that a good mix of survivability for the cohesive, copper adhesive and glass adhesive interfaces might be found with resin B. Experimental tests indicated that B had better interfacial qualities and was been selected for further study in applications. For instance, the B was used in a formulation which made use of both B and rearranged cross products of B and a cyanate ester. This formulation was tuned for a viafill application (the JM3200 series) and FIG. 9 shows the stress-cycling results of the four major cure components and their predicted cycling abilities. Using stress cycling analysis as well as adhesion analysis, the catalysis of this formulation was adjusted to try to maximize of best performing cure components (components 1 and 2) and to minimize the worst (components 3 and 4).

According to our panel testing when the catalysis was tuned correctly, this viafill showed superior robustness compared to other leading viafill formulations. This is shown in the cross-sections found in FIG. 6 where our viafill material is intact after 500 cycles Condition B thermal cycling, whereas competitor materials began to show cracking (middle figure) and degradation (left figure) after only 200 cycles.

Example 2

Figure 10:
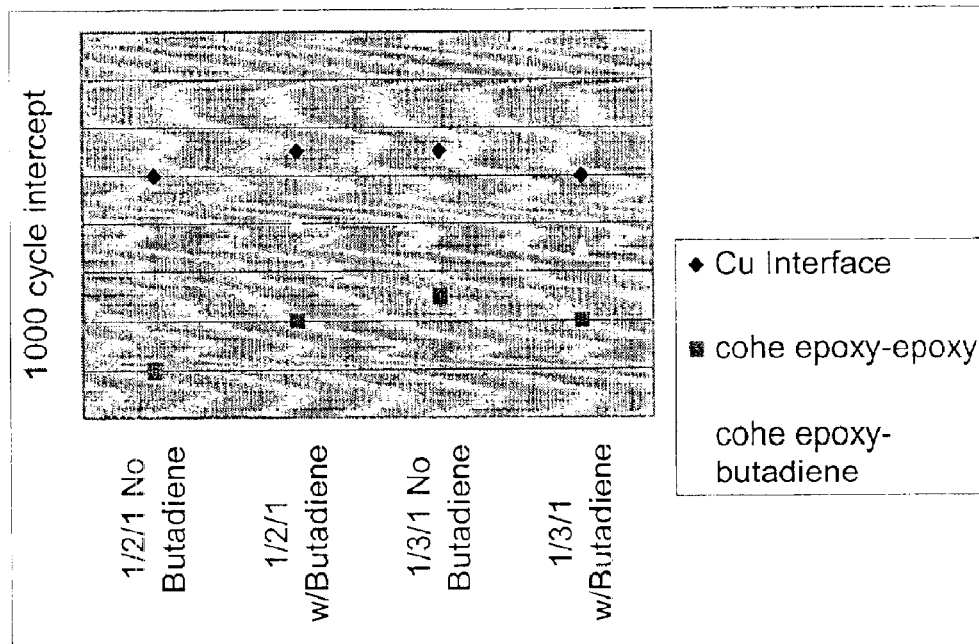
FIG. 10 is a graph of cycling results of a rubber modification.

It is commonly thought that moving failure toward the cohesive bulk and away from the adhesive interface was one way of controlling delamination. For instance, a benchmark formulation study was done on a melamine/novolac/bis A epoxy mixture. FIG. 10 shows that rubber seemed to enhance formulation of melamine/novalac/bisA cycling because of the presence of the epoxy-rubber interface (triangle points). Note that these melamine/novalac/bisA epoxy formulations were being provided by a commercial vendor (Shipley), and we were consistently having problems with cohesive failure. It is obvious then that this analysis also allows one to study stoichiometric effect (the 1/2/1 and 1/3/1 represent the ratios of melamine/novolac/bisA epoxy used, as parametric guesses based upon the Shipley MSDS's) as well as the effect of additive resins.

Figure 11:
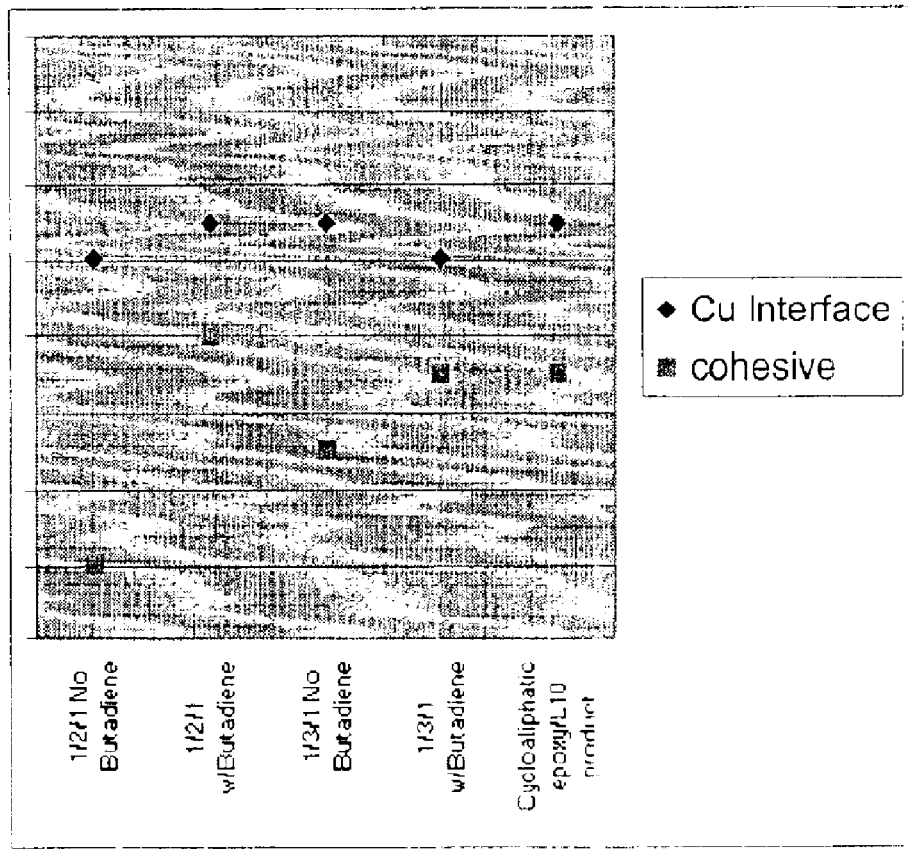
FIG. 11 is a graph showing several viafill formulations versus a 1000 cycle intercept as a function of a Cu interface (polymer/substrate interface) and a cohesive interface (polymer/polymer interface).
Figure 12:
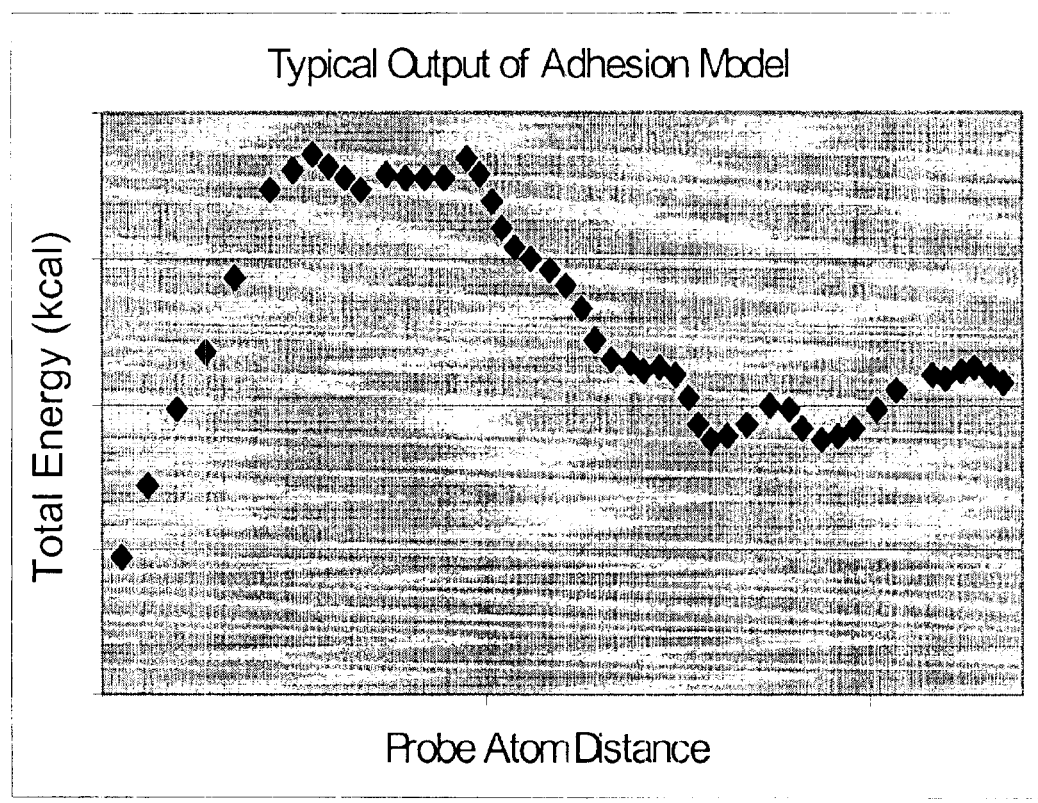
FIG. 12 shows a typical energy trajectory of a forcing dynamics run.

A second piece of experimental data was obtained by our own internal viafill formulations and is shown in FIG. 11. They consisted of L-10/cycloaliphatic epoxy formulations, and appeared to undergo thermal cycling quite well without failure (L10 is also known as 1,1 bis [4-cyanatophenylethane] available from Ciba-Geigy.) The formulations were patented in two applications: Ser. No. 09/133,507 ("Long and Short Chain Cycloaliphatic Epoxy Resins with Cyanate Ester") for the general formulation, and under Docket J104:33337 Entitled "Viafill Formulations which are electrically and/or thermally conductive or nonconductive" for the viafill. The cycling ability according to the cycling models was as good as the rubber modified melamine/novolac/bisA formulations (far right example in graph).

Because of these correlations to the already established formulations, additional possible formulations were sought where the cohesive strain cycling was close or better than the rubber enhanced melamine/novolac/bisA formulations as a benchmark. So far the modeling has shown 6 possible systems with adequate cohesive cycling (A-F).

Figure 13:
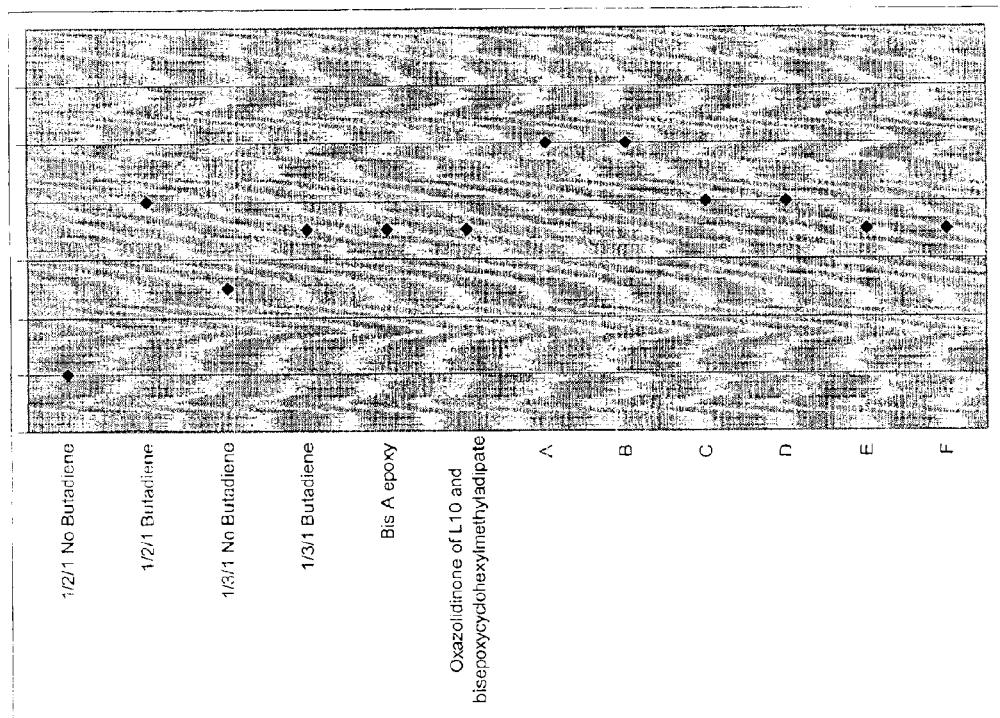
FIG. 13 is a graph showing several novel formulations versus a 1000 cycle intercept as a function of a cohesive interface (polymer/polymer interface). A is the product between trihydroxyethylisocyanurate and trisepoxypropyl isocyanurate; B is the product between trisepoxypropyl isocyanurate and oxydianiline; C is the product between trisepoxypropyl isocyanurate and bisphenol A epoxy; D is the product between trisepoxypropyl isocyanurate and oxybiscyclopentene oxide; E is the product between trihydroxyethylisocyanurate and trihydroxyethylisocyanurate; and F is the product between oxybiscyclopentene oxide and bisphenol A epoxy.
Figure 14:
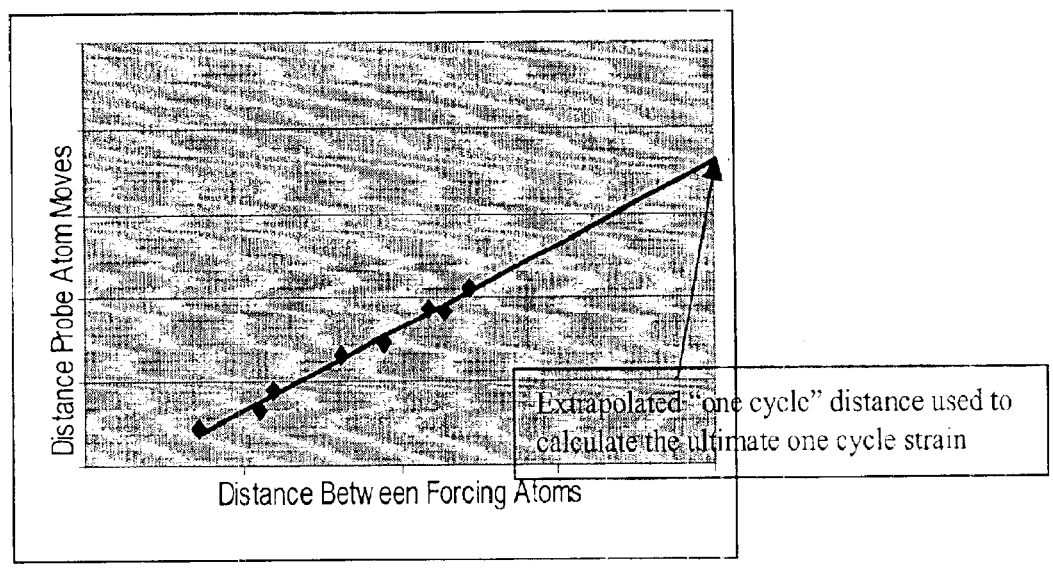
FIG. 14 shows an example of the extrapolation used to determine the distance a probe atom would move at ultimate one-step failure.

The strain direction used in the stress cycling method is very important and is determined through a large strain adhesive model (FIGS. 13 and 14). The polymer is forced off of its substrate in various directions in relationship to the substrate, and the highest energy direction is determined. Usually, this is determined by the activation energy determined in by the model (the highest energy obtained minus the initial energy).

In addition, the following steps are taken:

A. The stress vector is used which goes through the highest amount of the material (usually through the bulk of the polymer).

B. Usually a shear direction is used where there is more interaction with the substrate or other polymer over the length of the polymer(s) and which will lead to longer cycling runs than a stress direction which is orthogonal to the bulk of the polymer. The shear direction is preferred when there are no known orientational restrictions.

C. Crosslink points are very important especially if you are using a resin like an epoxy (which has a high probability of crosslinking). If there is a high possibility of crosslinking, it is important to use this as the base-polymer model, rather than a straight chain. If the polymer is loosely crosslinked, both models should be run to determine the extent of importance to cycling.

D. A preferred forcing atom is used, rather than a molecule or atom clusters. The preferred forcing atom is usually at the end of an oligomer, or close to a crosslink, depending upon the minimized conformation of the polymer how it orients to the substrate and the forcing direction used. That is sometimes it flattens out next to the substrate, and an end atom can be used; sometimes it "balls" up and a crosslink point is chosen. The final choice of the forcing atom (probe atom) is usually made by the initial adhesion models run to determine stress direction.

E. Normalization and determination of relative strain: This is another quirk of the method in order to obtain results that are comparable from system to system. The preferred method at this time is to calculate the strain obtained by the using the distance that the probe atom is moved by the total length of the polymer. The normalized strain is obtained by further normalization by the cross-section of the active atoms (usually the chain). Other normalization schemes have also been used, and it is important to be consistent.

In order to compare different systems in the Coffin-Manson correlation, the strain is normalized by the cross-section (previously mentioned) and also by the one-step ultimate strain (FIG. 14), which is determined by extrapolation. The extrapolation is done using the data obtained in the one step adhesion models (the ones used to determine stress direction and probe atom definition). Since the forcing vector is defined by two atoms (for example for a substrate and polymer, one atom on the substrate and one atom on the polymer), the distance between the forcing atoms and the distance the probe atom on the polymer moves is plotted. The line is extrapolated to ultimate failure defined by when the substrate and polymer separate, then the distance the probe atom moves is used to calculate the ultimate one step strain. See (FIG. 14).

The presence of a molecular mechanism to help explain stress response is significant because it indicates a basic relationship to performance on a molecular level. Such models could help the engineer understand the basic material weaknesses and help him implement correct process procedures.

Thus, specific embodiments and applications of polymer/substrate interfaces, their uses in electronic components and devices, and methods for selecting and forming such interfaces have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A method of forming an interface between a first polymer and a substrate comprising:

modeling a plurality of structural characteristics of a plurality of candidate interfaces by calculating a strain required to separate the first polymer from the substrate for each of the plurality of candidate interfaces over at least 1000 strain cycles;

selecting a relatively superior interface from the plurality of candidate interfaces;

obtaining a plurality of materials required to produce the first polymer and the substrate;

using the plurality of materials to produce the first polymer and the substrate; and coupling the first polymer and the substrate to form the interface.

2. The method of claim 1, wherein the first polymer comprises a monomer having the formula:

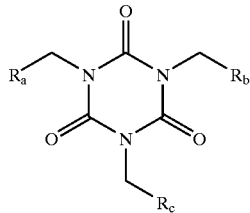

wherein each of $R_a$, $R_b$, $R_c$ are independently selected from the group consisting of a hydroxylated aliphatic side chain; an epoxy glycol; an ethoxy ether; a glycol ether; an adduct of glycol ether or a bisphenol glycol epoxy; an adduct of an epoxy glycol and an amine such as oxydianiline to form a hydroxylamine; an adduct of a glycol ether and a cycloaliphatic epoxy; or an adduct of hydroxyethyl side chain and a cycloaliphatic epoxy.

3. The method of claim 2, wherein the first polymer comprises an oxybis(cyclopentene oxide) group.

4. The method of claim 2, wherein the first polymer comprises an oxydianiline group.

5. The method of claim 2, wherein the first polymer comprises a bisphenol A glycidyl Epoxy group.

6. The method of claim 2, wherein the first polymer comprises a bis 3,4 epoxycyclohexylmethyl adipate group.

7. The method of claim 2, wherein the first polymer comprises a trishydroxyethylisocyanurate.

8. A method of forming an interface between the first polymer of claim 1 and a second polymer comprising:

modeling a plurality of structural characteristics of a plurality of candidate interfaces by quantitatively determining a strain required to separate the first polymer from a second polymer for each of the plurality of candidate interfaces over at least 1000 strain cycles; and selecting a relatively superior interface from the plurality of candidate interfaces;

obtaining a plurality of materials required to produce the first polymer and the second polymer; and using the plurality of materials to produce the first polymer and the second polymer;

coupling the first polymer and the second polymer to form the interface.

* * * * *